United States Patent [19]

Stafford et al.

[11] Patent Number: 5,331,550
[45] Date of Patent: Jul. 19, 1994

[54] APPLICATION OF NEURAL NETWORKS AS AN AID IN MEDICAL DIAGNOSIS AND GENERAL ANOMALY DETECTION

[75] Inventors: Richard G. Stafford, Chadds Ford, Pa.; Daniel J. Mickewich, Arden; Jacob Beutel, Hockessin, both of Del.

[73] Assignee: E. I. Du Pont de Nemours and Company, Wilmington, Del.

[21] Appl. No.: 16,343

[22] Filed: Feb. 11, 1993

Related U.S. Application Data

[63] Continuation-in-part of Ser. No. 664,906, Mar. 5, 1991, abandoned.

[51] Int. Cl.$^5$ ............... G06F 15/42; G06F 15/70; G06F 15/18
[52] U.S. Cl. ............... 364/413.02; 364/413.13; 395/11; 395/22; 395/924; 382/6; 382/14
[58] Field of Search ............... 364/413.13, 413.01, 364/413.02, 413.14; 382/6, 14, 15, 27, 30, 54; 395/21, 23, 924, 22

[56] References Cited

U.S. PATENT DOCUMENTS

| | | | |
|---|---|---|---|
| 4,323,973 | 4/1982 | Greenfield | 382/6 |
| 4,437,161 | 3/1984 | Anderson | 364/413.23 |
| 4,731,865 | 3/1988 | Sievenpiper | 382/54 |
| 4,736,439 | 4/1988 | May | 382/54 |
| 4,747,156 | 5/1988 | Wahl | 382/54 |
| 4,839,807 | 6/1989 | Doi et al. | 364/413.13 |
| 4,965,725 | 10/1990 | Rutenberg | 364/413.1 |
| 5,046,020 | 9/1991 | Filkin | 395/23 |
| 5,157,733 | 10/1992 | Takeo et al. | 382/6 |
| 5,245,672 | 9/1993 | Wilson et al. | 382/9 |
| 5,260,871 | 11/1993 | Goldberg | 364/413.02 |
| 5,267,151 | 11/1993 | Itam et al. | 364/413.09 |

OTHER PUBLICATIONS

Conference: Car '91 Computer Assisted Radiology, (published by Springer-Verlag, Berlin, Germany), pp. 289-294, Penedo et al., "A multi-layered neural network for the recognition of lung nodules on digital chest radiographs".
Am. J. Pathol., 95 (4 Suppl. 1), 1991, pp. 29-37, Dawson et al. "Nuclear Grading of Breast Carcinoma by Image Analysis Classification by Multivariate and Neural Network Analysis".
IEEE, Cat. No. 88CH2632-8, pp. 561-568, 1988 from IEEE Inter. Conf. on Neural Networks, Jul. 24-27, 1988, San Diego, Calif., Egbert et al. "Preprocessing of biomedical images for neurocomputer analysis".
Conference: INNC 90 Paris: International Neural Network Conf., Jul. 9-13, 1990, pp. 71-74, vol. 4 (published by Kluwer, Dordrecht, Netherlands), Anthony et al., "The use of neural networks in classifying lung scintigrams".
Pattern Classification Using Neural Networks, IEEE Communications Magazine, Nov. 1989, pp. 47-64, R. P. Lippmann.
Learning Internal Representation by Error Propagation, Parallel Distributed Processing: Explorations Microstructure of Cognition, vol. 1, MIT Press, Cambridge, Mass. (1986), chapter 8, pp. 319-362, Rumelhart et al.
Automated Analysis for Microcalcifications in High Resolution Digital Mammograms, Laura N. Mascio, Jose M. Hernandez and Clinton M. Logan, presented at Medical Imaging Feb. 1993, Newport Beach, Calif. pp. 1-8.

Primary Examiner—David M. Huntley

[57] ABSTRACT

A method for computer-aided detection of anomalies in an image comprise the steps of: (1) dividing the image into a plurality of m×n regions; (2) subtracting the background from each of the regions; (3) for each of the regions, selecting a smaller p×q subregion; (4) normalizing the p×q subregion; (5) feeding the p×q subregions into a neural network system, the neural network system having plural member neural networks, each trained to recognize a particular preselected anomaly type; (6) comparing each output value of the plurality of member neural networks to a first threshold; (7) selecting a maximum value from the output values which are greater than the first threshold; (8) comparing the maximum value to a second threshold above which the presence of an anomaly is indicated, and storing the result; (9) clustering a plurality of the stored results to form clusters; and (10) marking the location of the clusters.

8 Claims, 3 Drawing Sheets

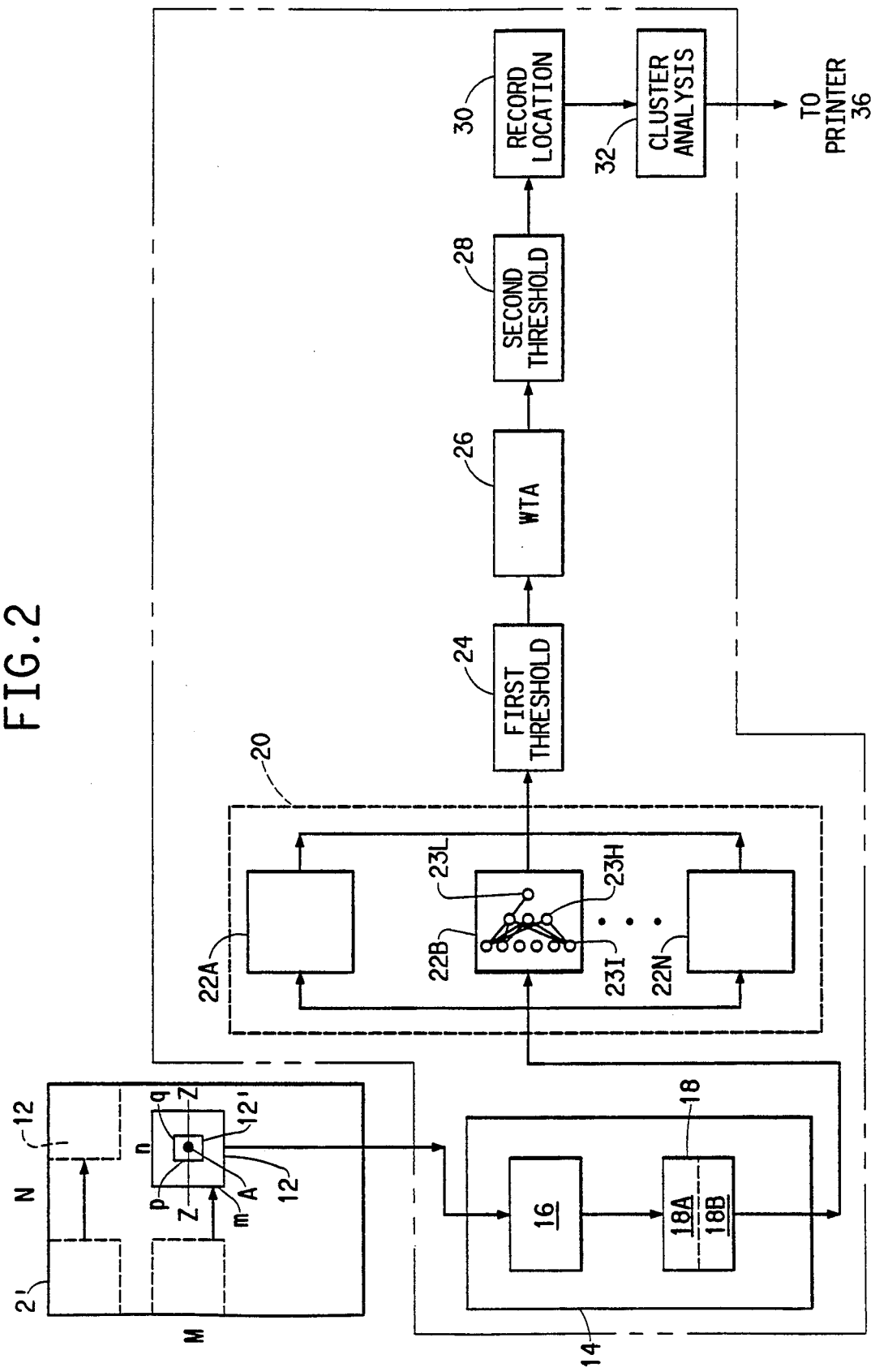

APPLICATION OF NEURAL NETWORKS AS AN AID IN MEDICAL DIAGNOSIS AND GENERAL ANOMALY DETECTION

CROSS REFERENCE TO RELATED APPLICATIONS

This application is a continuation-in-part of application Ser. No. 07/664,906, filed Mar. 5, 1991, now abandoned.

BACKGROUND OF THE INVENTION

1. Field of the Invention

The present invention relates to the computer-aided analysis of digitized images and, in particular, to the location of possible anomalies in medical diagnostic and/or industrial images.

2. Description of the Related Art

It has become an established and wide-spread medical practice to perform mammograms to determine the possible presence of breast cancer or other pathological conditions. The amount of time spent by health care professionals in scanning a large number of screening exam images tends to be very short and statistics indicate that diagnostic accuracy may suffer. Also, some features of these radiological images are such that their significance can only be recognized by specialized experts.

While diagnostic uncertainty may not exist in those instances in which a tumor or cancerous tissue is well developed and, thus, clearly visible to all, it will be appreciated that in the very early stages of the development of such tissue abnormalities, a reliable diagnosis based upon a brief examination of radiological images is much more difficult. Yet early diagnosis is a very important factor in arresting and effectively treating cancerous tissues and tissues which exhibit conditions precursory to cancer, particularly breast cancer.

In addition to the benefits of early determination of pathology in medical diagnostic images, such as mammograms, many types of defects in industrial images must also be detected during product manufacture to prevent catastrophic failure, e.g. in airplane turbine blades. Many types of anomalies in industrial materials have been identified and classified by computer analysis of an X-ray image. For example, in some cases, metal cracks or incomplete welds have precisely identifiable characteristics which may be programmed into a standard algorithmic computer for automated analysis. However, in most cases they cannot. Still other types of defects, such as corrosion pits and delaminations in honeycombed or layered materials, are even more difficult to characterize due to their variety of manifestations.

Both the medical diagnostic images and the latter variety of industrial x-ray images are not easily and simply classifiable and do not lend themselves to precise programmable characterizations, such as an expert system. Conventional algorithmic computers excel in applications where the knowledge can be readily represented by means of an explicit set of rules, e.g. a decision tree. Where this is not the case, conventional computers encounter difficulty. While conventional computers can execute an algorithm much more rapidly than any human, they are challenged to match human performance in nonalgorithmic tasks such as visual pattern recognition.

However, parallel distributed processing networks, also known as "neural networks", have been shown to be useful in recognizing patterns in a number of applications involving multiple variables whose precise interactions are not well-understood or quantifiable.

In contrast to algorithmic computer systems (including so-called "expert systems"), a neural net computing system is not formulated to exhibit an explicit algorithm or a set of explicit rules. Instead, a neural network is "trained" to recognize patterns in input data by an iterative adjustment of the connection weights associated with each processing element. These connection weights are adjusted to minimize a preselected output error function. This adjustment of the weights may be accomplished by various well-known techniques.

In traditional image analysis (and/or processing), background subtraction and image normalization have been used to obtain better image resolution with reduced noise. However, when at least some of the areas of interest in the data are sufficiently close to the noise, removal of background from the entire image and subsequent normalization may not satisfactorily distinguish such data from the overall noise. There is thus a need in image analysis for an improvement in the separation of various areas of interest from the effects of overall noise in the image.

SUMMARY OF THE INVENTION

The present invention employs analysis by a parallel distributed processing system to accurately provide information about the location of possible anomalies in medical diagnostic and industrial images.

The invention is more particularly described as a method for computer-aided detection of possible anomalies in a digitized image comprising a plurality of $M \times N$ picture elements each representing an optical density in the digitized image, the method comprising the steps of:

a) subdividing the digitized image into a plurality of predetermined regions each comprising $m \times n$ picture elements, where $m < M$ and $n < N$;

b) subtracting background from each predetermined region of the digitized image;

c) selecting a subregion comprising $p \times q$ picture elements, where $p < m$ and $q < n$;

d) normalizing the image data from the $p \times q$ subregion;

e) using a neural network system, analyzing each predetermined subregion of the digitized image to recognize any pattern indicative of an occurrence of a possible anomaly, the neural network system comprising at least two member neural networks each trained to recognize a particular preselected anomaly-type of a preselected size and to produce an output signal value indicative of the presence of said preselected anomaly type;

f) comparing the output values of each of the member neural networks to a first predetermined threshold value above which the presence of a possible anomaly is indicated;

g) comparing the output values that exceed the first threshold(s) to select the maximum signal value;

h) comparing the maximum signal value to a second predetermined threshold value above which the presence of a possible anomaly is indicated;

i) based upon these comparisons, determining the location within the digitized image of each possible anomaly;

j) using a clustering analysis, identifying each vicinity on the digitized image at which a cluster of locations of possible anomalies occurs; and, k) marking the location on an original image corresponding to the digitized locations of the clusters.

BRIEF DESCRIPTION OF THE DRAWINGS

The invention will be more fully understood from the following detailed description thereof, taken in connection with the accompanying drawings, which form a part of this application and in which:

FIG. 2 is a more detailed block diagram of the analysis executed by a digital computer operating in accordance with a program in accordance with the present invention;

FIG. 3A is a plot of optical density values versus distance along a line Z—Z in the digitized image of FIG. 2, while

DETAILED DESCRIPTION OF THE INVENTION

Figure 1:
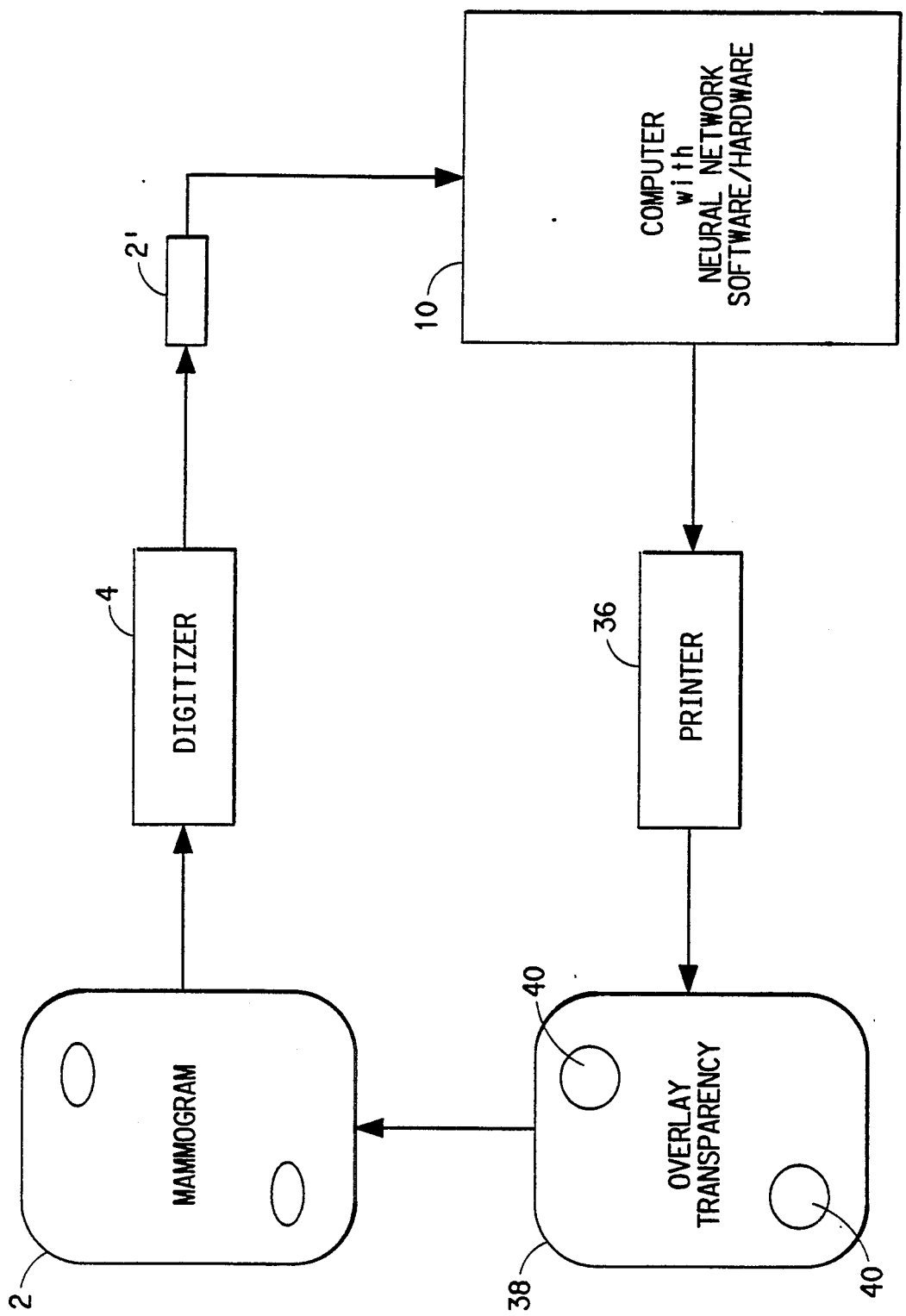
FIG. 1 represents a block diagram of the overall process in accordance with the present invention.

Throughout the following detailed description, similar reference numerals refer to similar elements in all Figures of the drawings.

The present invention, illustrated by an overall block in FIG. 1, relates to a method of computer-aided analysis of an analog image 2 to determine the presence of anomalies therein. The anomalies are indicted by the reference character A. Although the analog image 2 is indicated as an x-ray film containing a medical diagnostic image such as a mammogram, it should be understood that the invention may be used with any form of medical diagnostic image containing possible pathologies, such as X-ray images, computerized axial tomography (CAT) scans, positron emission tomography (PET) scans, magnetic resonance images (MRIs), and sonogram images. In addition, the invention may be applied to detect defects in various industrial images, such as radiographs or sonogram images of parts, equipment, and/or welds. It is noted that, as used herein, the term "anomaly(ies)" is meant to encompass within it the terms "pathology(ies)" and "defect(s)".

As a first step the analog image 2 is raster-scanned and digitized by a digitizing apparatus 4, such as a scanning laser digitizer 4. The resultant digitized output image 2' from the digitizer 4 comprises a matrix of M rows by N columns (M×N) of adjacent individual picture elements ("pixels"). In a typical medical diagnostic application of the invention the digitized image comprises a matrix on the order of four thousand by four thousand five hundred (4000×4500) pixels. Each element in the M×N matrix is an optical density value.

Scanned pixel sizes generally range in size from ten micrometers (10 μm) to two hundred micrometers (200 μm). For medical images, such as a mammogram, the scanning aperture of the digitizer 4 is chosen to produce pixels on the order of thirty micrometers (30 μm) to seventy micrometers (70 μm), and more preferably, fifty micrometers (50 μm).

In medical or industrial applications where an image 2' may pre-exist in a digital format, as in the case of some digital modalities such as PET scans, CAT scans, MRIs and sonograms, scanning to digitize the image is not required.

The digitized image 2' from the digitizer 4 is submitted for image analysis to a digital computer 10 operating in accordance with this invention. The digitized image 2' may be stored temporarily in a memory buffer in the digitizer 4 and then transferred to the memory of the computer 10 or may be immediately transferred and stored in the memory of computer 10. The digitized image 2' is stored as an M×N matrix of optical density values representing the sampled adjacent pixel locations in the image 2'.

A more detailed block diagram of the analysis steps executed within the computer 10 is shown in FIG. 2. For analysis purposes the digitized image 2' from the digitizer 4 is subdivided into a predetermined number of regions, each of which contains a matrix of m rows by n columns (m×n), where m<M and n<N. In the preferred embodiment, the matrix defining each region of the image is on the order of sixty four by sixty four (64×64) pixels.

In the preferred case, as is suggested in FIG. 2, each matrix representing a region of the overall digitized image 2' may be envisioned as being generated as the result of the raster scan of an m×n (64×64) pixel "window" 12 moving across the digitized image 2'. Starting from the upper left hand corner of the image 2' the window 12 may be horizontally incremented across the image 2' by any convenient predetermined number of pixels. Preferably, the window 12 is incremented one pixel at a time. Similarly, at the end of each horizontal scan, the window 12 is vertically incremented by any convenient predetermined number of pixels (again, preferably, one pixel at a time).

In some instances, to minimize the digital computational requirements and the analysis time required for interpretation, the original digitized image is subjected to segmentation analysis to identify the image within the window. The output of this process is the set of pixel coordinates defining the boundary of the image which determines the region of interest for further image processing. Raster scanning is then performed only over the region of interest defined by the segmentation analysis process.

Each subdivided region of the image 2' as defined by the window 12 is preprocessed in preparation for analysis, as generally indicated by the block 14. In one aspect image preprocessing 14 includes background subtraction, as indicated at 16. Another aspect of image preprocessing is a two-stage normalization, as indicated at 18.

After image preprocessing, image analysis is performed using a parallel distributed processing system ("neural network system") 20 comprised of a plurality of at least two, or more, trained member parallel distributed processing networks 22 ("neural networks").

Figure 3A:
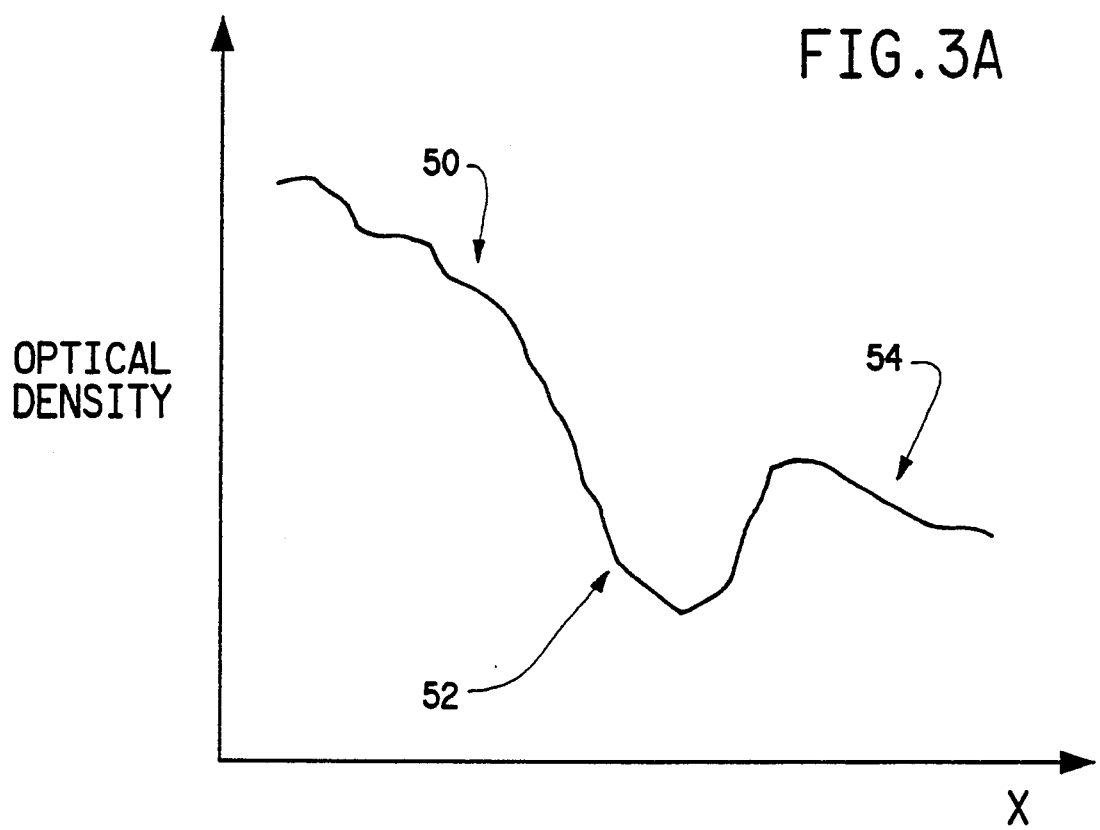
Figure 3B:
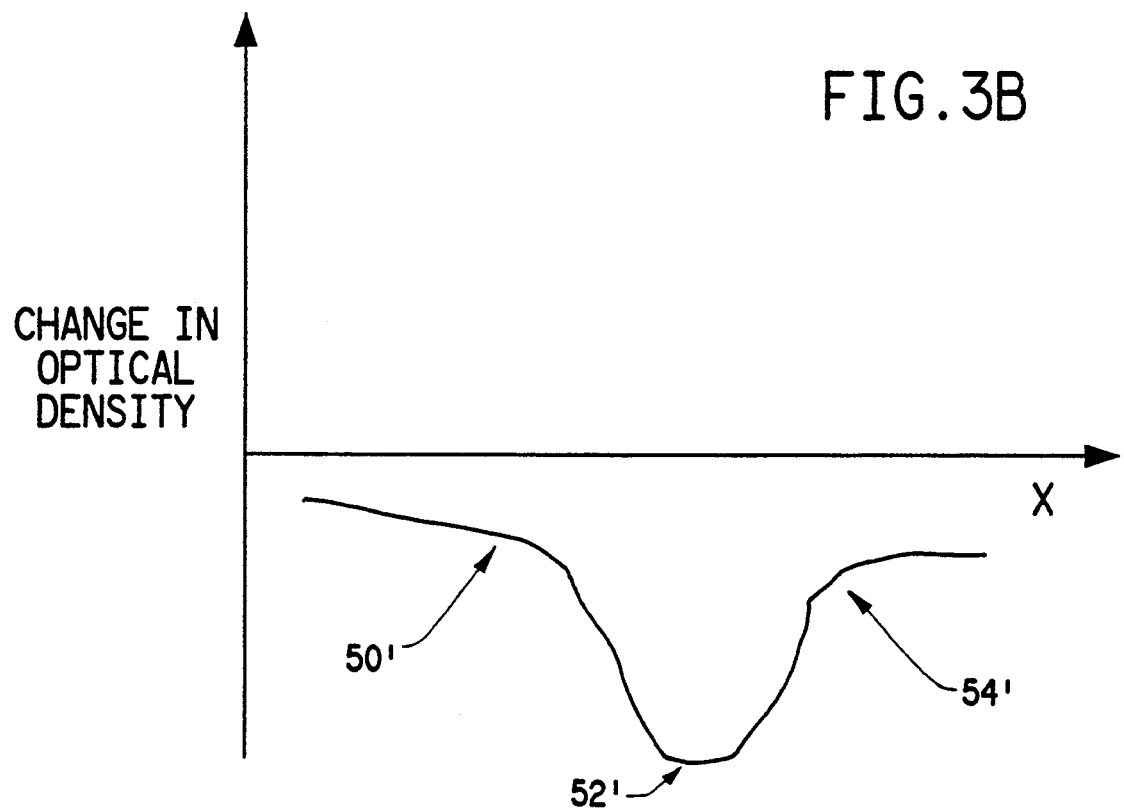
FIG. 3B is a representation of the plot of FIG. 3A following background subtraction.

Background subtraction is performed to narrow the range of optical density information that must be analyzed. As seen in FIG. 2, one region of the image 2' as defined by the matrix window 12 is shown to contain an anomaly A. FIG. 3A is a plot of the optical density values versus distance along the line Z—Z extending through the window with the anomaly A therein. Sections 50 and 54 of the plot of FIG. 3A show a gradual decrease in optical density readings across the window 12. Section 52 of the plot represents a significant change in optical density due to the presence of the anomaly A. After background subtraction, as seen in FIG. 3B, sections 50' and 54' respectively represent the leading and trailing sections 50, 54 of the original plot (FIG. 3A), while section 52' represents the optical density difference of the anomaly A.

Any one of a number of ways of background subtraction from a data sample known in the art may be used. For example, the "least squares" approach may be used. For each pixel position in the region defined by the window 12 a plane is fitted by a least-squares algorithm to all of the pixels within the window:

$$\overline{D_{i,j}} = a_0 + a_1 i + a_2 j$$

where $\overline{D}_{i,j}$ is the estimated pixel value at the position (i,j) in the sixty-four by sixty-four pixel window 12 and the coefficients ($a_0$, $a_1$, $a_2$) are obtained by least-squares fitting. The estimated planar fit is then subtracted from the original pixel value in the upper left hand pixel closest to the window center:

$$\Delta D_{i,j} = D_{i,j} - \overline{D_{i,j}}$$

where $D_{i,j}$ is the original pixel value at (i,j). The resultant pixel value (optical density difference, $\Delta D_{i,j}$) is then stored in a secondary image at its respective coordinates.

Through use of the least squares plane the background may be subtracted from the original optical density values of matrix window 12.

In the preferred embodiment, the area of the anomaly A should be significantly smaller than the area of the region of the image 2' defined by the window 12. For example, a window 12 may be sized so that the largest pathology or defect examined would be perhaps a factor of ten times smaller than the window 12. In such a case most of the pixels are associated with the background. Thus, in effect, a high-pass spatial frequency filtering operation is performed. When the least squares plane is subtracted, the optical density values in the region of interest increase in proportion to the background optical density values and, thereby, the signal to noise ratio is improved (FIG. 3B).

Following background subtraction a subregion 12' of p×q pixels, where p<m and q<n, is selected from within the m×n region 12, preferably from the center thereof. In the preferred case subregion 12' is on the order of sixteen by sixteen pixels. As indicated at 18 in FIG. 2, a two-stage normalization operation is then performed on the pixels in the subregion 12', The first normalization stage is a scale invariance transformation 18A. When imaged, a specific anomaly will exhibit quantitatively different spatial optical density profiles depending on different exposure conditions, film sensitivities, and film sensitometries. To reduce the computational classification requirements for pattern recognition of suspect anomalies, a normalization procedure is required for identifying anomalies of the same type, regardless of image capture conditions. In addition, even if the exposure conditions, film sensitivities, and film sensitometries are the same, there are classes of anomalies that exhibit different optical density profiles, which, after undergoing a linear transformation, will exhibit the same normalized spatial profile. Again it is advantageous to consider such anomalies as belonging to the same class. A straightforward method for performing this classification normalization is by transforming the vector quantized image onto a unit sphere in n-dimensional pixel space for each p×q window to be analyzed for the presence of an anomaly. A specific anomaly shape class is then recognized by its phase angle in this normalized n-dimensional space.

The high-pass filter image undergoes a second raster scan using the smaller p×q window 12'. Using a fifty micrometer (50 μm) pixel scanning aperture diameter this smaller (16×16) pixel window 12' is sufficient to allow anomalies of approximately fifty to two hundred fifty micrometers (50–250 μm) diameter to be recognized. The upper left hand pixel nearest the center of the window is again tagged. All of the pixels within this window are assumed to form an orthogonal vector space of two hundred fifty six (256) dimensions, where each dimension represents the range of possible preprocessed optical densities ($\Delta D_{i,j}$ values) for its respective pixel. All pixel values within the window are linearly transformed to fit the normalized range of zero to one:

$$\sum_{i,j=1}^{16} (\Delta D_{i,j})^2 = 1; \theta_{i,j} = \cos^{-1} \Delta D_{i,j}$$

where $\theta_{i,j}$ is the direction arccosine of the normalized pixel value at (i,j). The spatial shape of an object within the original window is now encoded as a phase angle vector, $\theta$, within this 256-dimensional vector space and the tip of each vector representing an object lies on a unit sphere.

The second normalization stage 18B is a dynamic range normalization, wherein the set of transformed optical density difference values of the subregion 12' are normalized to fit the input dynamic range of each member neural network 22 in the neural network system 20. For example, if the functions employed in any hidden and output layers of the member neural networks yield values within the ranges of −1.0 to +1.0, the valises at the input layer should be normalized to fit within this range.

It should be noted that both the background subtraction 16 (performed on the region 12) and the two-stage normalization (18 performed on the subregion 12') are local to each predetermined region or subregion, as the case may be. Since background subtraction 16 and two-stage normalization 18 are performed locally, small changes within each region or subregion are not masked or hidden by the overall noise characteristics of the image 2'.

The actual anomaly recognition is performed using the neural network system 20 comprised of a plurality of at least two trained member neural networks 22A through 22N. Each member neural network 22A through 22N is, in the preferred instance, a feedforward neural network having at least three layers, an input layer 23I, an intermediate or "hidden" layer 23H, and an output layer 23L. Each node in each layer is connected through connection weights to every node in an adjoining layer. A three-layer neural network is the minimum network topology required to obtain an arbitrary nonlinear mapping of input to output. Each input and hidden layer 24I and 24H, respectively, in each member neural network 22A through 22N is comprised of a plurality of nodes. Each output layer 24L in each member neural network 22A through 22N is comprised of one or more nodes. Each member neural network 2A through 22N should be fully connected.

Each node, or processing element, in the input layer has, as its input, a stored digital value representing the preprocessed values of each element in the subregion 12'. Each node in each succeeding layer has as its input the signal present at the output of the nodes of an adjoining layer, as multiplied by their associated connection weights. Each node has a constant bias input, or offset, value which is multiplied by its own weighting factor. The inputs to each node are summed and scaled by a nonlinear transformation to produce an output signal value. In the preferred case the hyperbolic tangent function, whose output range is −1 to +1, is employed as the nonlinear function. The topology, structure, and organization of a three-layer neural network is fully discussed in U.S. Pat. No. 5,046,020 (Filkin), which is hereby incorporated by reference.

Each member neural network 22A through 22N is trained to recognize a particular anomaly type and/or size. For example, in the analysis of mammograms, a subsystem comprising one or more member neural network(s) 22 detects a first anomaly type, such as a microcalcification, while a second subsystem comprising one or more other member neural network(s) may be trained to recognize a second anomaly type, such as a lesion. Furthermore, each subsystem of member neural networks 22 may detect a given type of anomaly whose size falls within particular predetermined size ranges, e.g. fifty (50 $\mu$m) to one hundred micrometers (100 $\mu$m), one hundred micrometers (100 $\mu$m) to one hundred fifty micrometers (150 $\mu$m), etc. Such a grouping of member neural networks to detect various sizes of an anomaly of a given type provides a measure of redundancy in detecting that particular anomaly type and, thereby, adds significantly to the accuracy of the results.

Training may be accomplished using the back propagation paradigm as discussed in "Parallel Distributed Processing", D. E. Rumelhart, G. E. Hinton, and R. J. Williams, Volume 1, Chapter 8, "Learning Internal Representations by Error Propagation", Bradford Books, 1986. The software package ANSim, version 2.30 (©1988, Science Applications International Corporation, San Diego, Calif.), may be employed for this purpose. Alternately, the training method disclosed in U.S. Pat. No. 5,046,020 (Filkin), assigned to the assignee of the present invention, wherein the connection weights are generated using stiff differential equations may be used.

As is well understood by those skilled in the art, training of each member neural network uses a "training set" containing an adequate sampling of digitized images of regions of analog images that either manifest an anomaly of interest or that are anomaly-free. A record is kept correlating the digitized sample images to their location in the original analog images. In addition, in the preferred embodiment, a value is stored with each training sample to indicate whether an anomaly is present (e.g. +1.0) or to indicate that a window is anomaly-free (e.g. −1.0).

As the neural network is interpolative in nature, its level of accuracy when in ultimate use depends in large part on whether the data used in training the member neural networks is a statistically significant representative sampling. Some of the factors to consider in selecting a statistically significant number of samples to adequately train a member neural network to identify a particular anomaly include the type of anomaly, the variation in characteristics of the anomaly, the size of the neural network (number of weights, number of layers, number of nodes), and the noise in the analog images. However chosen, the number of samples in a training set must be a statistically significant number of samples having a particular characteristic (e.g. size, shape, intensity profile, etc.) to present to a neural network to allow it be adequately trained. "Adequate training" means trained to recognize an anomaly within a user-defined accuracy. Each neural network is separately trained to identify a predetermined size range of a predetermined type of anomaly, with all other member neural networks de-activated, so that a given member network will respond most strongly only when the characteristics that it has elicited from its training set are present in an image outside the training set.

The iterative process through which initial weight values are incrementally changed until the error in the output of the network ceases to be reduced significantly (i.e., a local minimum is reached) is discussed in the above-referenced U.S. Pat. No. 5,046,020 (Filkin) and need not be repeated here.

Once a member neural network is trained, testing of each member neural network must be undertaken to determine if the local minimum produced through training will satisfy desired accuracy requirements for anomaly identification. Testing will determine if further training of the various member neural networks is required.

As indicated in FIG. 2 at block 24, the output signal values of each member neural network is compared to a first predetermined anomaly threshold value above which the presence of a possible anomaly of the given type is indicated. Also, a user may define separate anomaly threshold values for each member neural network. Alternatively, a single threshold value may be defined to which the outputs of all member neural networks are compared.

Those output signal values exceeding the first threshold value(s) are compared to each other by a winner-take-all (WTA) algorithm 26 to select the maximum signal value. The output value selected by the WTA algorithm 26 is compared to a second predetermined threshold, above which the presence of a possible anomaly of the given type is also indicated. The comparison to the second threshold is shown in FIG. 2 at block 28. Depending upon the magnitude of the second threshold value the output of the thresholded WTA 26 may detect a fraction of image features which do not actually represent anomalies ("false positives") or may fail to detect a fraction of image features which do actually represent anomalies ("false negatives"). The second threshold must be larger than or equal to the minimum value of the first threshold(s).

In assigning either of the thresholds 24 or 28 it should be noted that the lower its value, the higher is the number of false positives. Conversely, the higher the threshold values the greater the possibility of yielding false negatives. For example, given an output range of −1.0 to +1.0, a user may set the threshold for detecting a particular anomaly at +0.3. If the single value from the WTA algorithm 26 exceeds +0.3, a particular anomaly type may be present within subregion 12', e. g., 95% of the time. That is, in 95% of cases a physician's diagnosis will agree that the neural network detected a particular pathology. If greater accuracy is needed, the threshold level may be adjusted higher, e.g. to +0.4, during network training to achieve, say, 98% accuracy. However, the false negative rate will also increase. That is, a number of actual pathologies having presented output signal values between +0.3 and +0.4 will now remain undetected at the higher threshold value.

As indicated at block 30 in FIG. 2 if an anomaly is detected the location within the subregion 12' containing the anomaly is recorded for future analysis. In the preferred embodiment, the location of the subregion 12' is defined by the coordinates of the pixel in the upper left hand corner.

Each scan of the regions of the image defined by the stepwise raster scanning of the window 12 is analyzed in the manner discussed until either the entire digital image or the region of interest defined by the segmentation process has been examined. After the entire image has been thus analyzed by the neural network system, the coordinates of all detected possible anomalies are transmitted to block 32 for further analysis. For instance, a two-stage clustering analysis algorithm may be applied which detects the presence of a predetermined number (e.g., more than three) of possible anomalies within a predetermined radius.

The two-stages of the clustering analysis include microclustering binding and macroclustering binding. Microclustering binding of the thresholded image is required to remove multiple counts of the same anomaly. Since the nonlinear convolution transform in the second scan involved the $p \times q$ ($16 \times 16$) window 12', microclustering requires a third image raster scan with the same window size. All locations in which an anomaly occurs within the window are interpreted as belonging to the same anomaly. A final map is then generated, representing the location of all recognized individual anomalies in the image.

The interpretive significance of anomalies within the image 2 depends on many factors, but one of primary significance is related to the number of anomalies within an area of specified size. Macroclustering accepts the possibility of an anomaly when at least four positive events are detected within a diameter of approximately one centimeter. This filtering operation eliminates single anomalous events due to highly localized film defects and questionable interpretations of events associated with the detection of anomaly sizes at the minimum spatial resolution of the film digitizing system.

The final scan of the image with this macroclustering criterion generates the final map representing regions of interest in which possible anomalies have been detected. Due to the stochastic distribution of anomaly occurrences within a specific image 2 the boundary lines enclosing these regions of interest can be irregular and can extend beyond the one centimeter diameter threshold.

With reference again to FIG. 1, if at least one cluster of anomalies is detected a signal is sent to a printer 36. The printer 36 produces a transparency overlay sheet 38 containing at least one marker 40 which, when superimposed upon the original image 2, calls a viewer's attention to the location of possible anomalies. In the preferred embodiment the marker 40 takes the form of a closed contour centered on the location of an anomaly. The positioning of the closed contour may be accomplished by a conventional center of mass technique.

If the analog image is digitized from a video signal, markers may be placed on an overlay transparency or a superimposable graphics layer to indicate the positions of suspected abnormalities on the video monitor displaying the original video image.

However, if the user is unable to achieve specified percentages of true positives and false positives from iterative training of the neural network, it may be necessary to select different initial weights, e.g. by choosing a new random weight vector. One might also increase the number of hidden layers to reduce the error percentage or increase the number of nodes in the hidden layer to further reduce the error.

An adequately trained neural network comprises a set of trained weights which meet the specified requirements for the incidence of false positives and false negatives.

Those skilled in the art, having the benefit of the teachings of the present invention as hereinbefore set forth, may effect numerous modifications thereto. Such modifications are to be construed as lying within the contemplation of the present invention, as defined by the appended claims.

What is claimed is:

1. A method for computer-aided detection of possible anomalies in a digitized image comprising a plurality of $M \times N$ picture elements each representing an optical density in the digitized image, the method comprising the steps of:

a) subdividing the digitized image into a plurality of predetermined regions each comprising $m \times n$ picture elements, where $m < M$ and $n < N$;

b) subtracting background from each predetermined region of the digitized image;

c) selecting a subregion comprising $p \times q$ picture elements, where $p < m$ and $q < n$;

d) normalizing the image data from the $p \times q$ subregion;

e) using a neural network system, analyzing each predetermined subregion of the digitized image to recognize any pattern indicative of an occurrence of a possible anomaly, the neural network system comprising at least two member neural networks each trained to recognize a particular predetermined anomaly type within a predetermined size range and to produce an output signal value indicative of the presence of said predetermined anomaly type;

f) comparing each of the output values of each of the member neural networks to a first predetermined threshold value corresponding to each member neural network above which the presence of a possible anomaly is indicated;

g) comparing each output value that exceeds each first predetermined threshold to each of the other output values that exceed each corresponding first predetermined threshold to select the maximum signal value;

h) comparing the maximum signal value to a second predetermined threshold value above which the presence of a possible anomaly is indicated;

i) based upon the comparisons of step h), determining the location within the digitized image of each possible anomaly;

j) using a clustering analysis on the locations of possible anomalies of step i), identifying each vicinity on the digitized image at which a cluster of locations of possible anomalies occurs; and, k) creating a marker for each cluster, having a contour that surrounds all of the anomalies in each cluster, corresponding to the digitized location of each cluster.

2. The method of claim 1 wherein the step k) itself comprises the step of placing the marker on a transparency overlay sheet.

3. The method of claim 1 wherein each subregion of $p \times q$ picture elements is selected from the center of each $m \times n$ region.

4. The method of claim 1 wherein the step b) comprises using a high pass spatial frequency filter.

5. The method of claim 1 wherein the step d) comprises using a two-stage normalization, the first stage being a scale invariance transformation, and the second stage being a dynamic range normalization.

6. The method of claim 1 wherein the step j) comprises using a two-stage clustering algorithm, the first stage being a microclustering binding step, and the second stage being a macroclustering binding step.

7. The method of claim 1 wherein each first threshold value of step f) is different for each member neural network.

8. The method of claim 1 wherein each first threshold value of step f) is the same for each member neural network.

* * * * *